Figure 1:
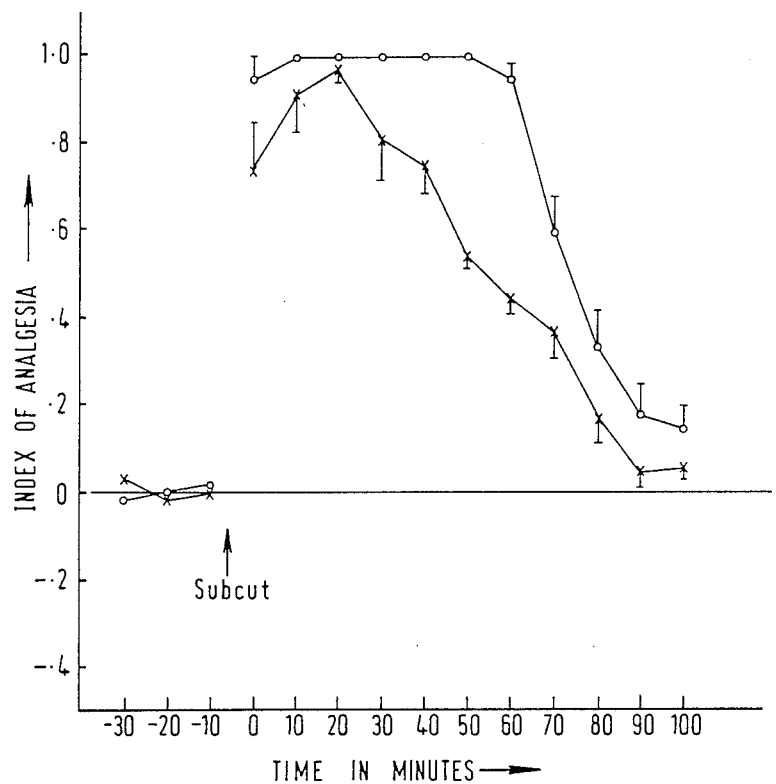

United States Patent [19]

Roberts

[11] Patent Number: 4,871,750
[45] Date of Patent: Oct. 3, 1989

[54] USE OF DIOXOPIPERIDINE DERIVATIVES AS ANALGESICS

[75] Inventor: Malcolm H. T. Roberts, Cowbridge, United Kingdom

[73] Assignee: National Research Development Corporation, London, England

[21] Appl. No.: 206,273

[22] Filed: Jun. 14, 1988

[30] Foreign Application Priority Data

Jun. 16, 1987 [GB] United Kingdom ................ 8714033
Jun. 19, 1987 [GB] United Kingdom ................ 8714374

[51] Int. Cl.[4] .......................................... A61K 31/445
[52] U.S. Cl. .................................................... 514/328
[58] Field of Search ........................................ 514/328

[56] References Cited

U.S. PATENT DOCUMENTS 4,461,771 7/1984 Gittos et al. ........................ 514/328

Primary Examiner—Stanley J. Friedman
Attorney, Agent, or Firm—Cushman, Darby & Cushman

[57] ABSTRACT

Phenyl-3-aminoalkyl-4-methyl-2,6-dioxopiperidines of the Formula I

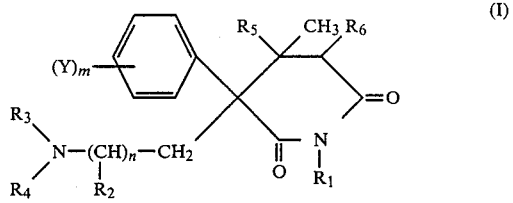

wherein:
$R_1$ represents hydrogen or $C_1$–$C_4$ alkyl;
n is 1 or 2;
$R_2$ represents hydrogen or methyl, provided that one $R_2$ is hydrogen when n is 2;
$R_3$ represents hydrogen or $C_1$–$C_2$ alkyl;
$R_4$ representss $C_1$–$C_2$ alkyl;
$R_5$ and $R_6$ independently represent hydrogen or methyl;
m is 0 to 3; and
each Y is in a meta or para position and independently represents hydroxy, $C_1$–$C_2$ alkoxy, $C_1$–$C_2$ alkyl, $C_1$–$C_2$ hydroxyalkyl, halogen, or trifluoromethyl, provided that hydroxy and alkoxy are not in the para position.

or pharmacologically acceptable acid addition salt thereof have analgesic activity. The compounds can be administered enterally, parenterally or topically. The topical compositions are novel.

The presently preferred compound is 3-(3'methoxyphenyl)-3-(3"-N,N-dimethylaminopropyl)-4,4-dimethyl-2,6-dioxopiperidine (AGN 2979).

15 Claims, 5 Drawing Sheets

FIG. 4. MORPHINE IN TOLERANT RATS

USE OF DIOXOPIPERIDINE DERIVATIVES AS ANALGESICS

This invention relates to the use of certain 3-phenyl-3-aminoalkyl-4-methyl-2,6-dioxopiperidines as analgesics. In particular, the invention provides the use of the said dioxopiperidines in the manufacture of analgesic medicaments, topical compositions comprising said dioxopiperidines, and methods of analgesic treatment using said dioxopiperidines.

Morphine in various forms has been used to suppress pain perception (i.e. as an analgesic) for about 3,000 years. Even today, morphine and related opioids remain the most potent and frequently used of the analgesics. However, these drugs have serious adverse side effects which limit their use. To varying extents, they are addictive, severely affect gut motility, and depress respiration to a dangerous degree. Further, patients becomed adapted to them requiring ever increasing doses to obtain relief. The drugs are abused by those who become addicted to them and hence their availability is restricted.

It will be appreciated from the above that there exists a long-established need for a strong analgesic which does not have the adverse side effects of the opioid analgesics. An object of this invention is to provide a class of analgesic compounds of which at least some do not exhibit said adverse side effects.

It has surprisingly now been found that certain 3-phenyl-3-aminoalkyl-4-methyl-2,6-dioxopiperidines (as defined hereinafter) have strong analgesic activity.

GB 1455687 (also AU 480855, BE 808958, DE 23630526, FR 7346904, JP 6053014 and U.S. Pat. No. 3963729) discloses that 3-phenyl-3-aminoalkyl-4- and/or 5-methyl-2,6-dioxopiperidine derivatives have central nervous system, especially antidepressant, activity. Said compounds include, inter alia, those of the following Formula A.

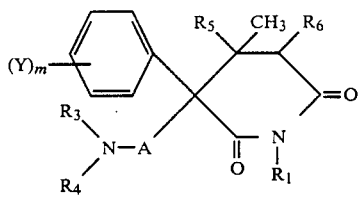

wherein:
$R_1$ represents hydrogen or $C_1$–$C_4$ alkyl;
$R_3$ represents hydrogen or $C_1$–$C_4$ alkyl;
$R_4$ represents $C_1$–$C_4$ alkyl;
$R_5$ and $R_6$ independently represent hydrogen or methyl;
A represents $C_1$–$C_6$ alkylene;
m is 0 to 3; and
Y is hydroxy, $C_1$–$C_4$ alkoxy, $C_1$–$C_4$ alkyl, $C_1$–$C_4$ hydroxyalkyl, halogen or trifluoromethyl.

It also has been disclosed in U.S. Pat. No. 4,461,771 that compounds of Formula A, in which $R_1$ represents hydrogen; $R_3$ and $R_4$ independently represent methyl or ethyl; $R_5$ represents methyl; $R_6$ represents hydrogen; A represents ethylene or propylene; m is 1 or 2; and each Y is in a meta position and independently represents hydroxy or $C_1$–$C_2$ alkoxy, are believed to reduce in vitro the activity of tryptophan hydroxylase by blocking the depolarization-induced activation of the enzyme in the brain stem and hence are of potential use in the prophylactic treatment of the stressful disorder migraine. More recently, it has been reported that at least one compound of Formula A (viz 3-(3'-methoxyphenyl)-3-(3''-N,N-dimethylaminopropyl)-4,4-dimethyl-2,6-dioxopiperidine; AGN 2979) also blocks in vitro the activation of tryptophan hydroxylase resulting from exposure of brain stem slices to metabolic inhibitors or methylxanthines or induced by incubation of supernatant preparations of the enzyme under phosphorylating conditions (Boadle-Biber, M.C. et al Biochem. Pharmacol. 35, 1521–6, (1986)). However, it also has been reported that AGN 2979 has no significant effect in vitro upon the unactivated enzyme (Boadle-Biber, M.C. et al supra).

Further, it has recently been disclosed in GB 2181346A that compounds of Formula A, in which $R_1$ represents hydrogen; $R_3$ and $R_4$ independently represent methyl or ethyl; A represents ethylene or propylene; m is 1 or 2; and each Y is in a meta position and independently represents hydroxy or $C_1$–$C_2$ alkoxy, are believed to reduce the turnover of 5-hydroxytryptamine (5 HT) resulting from inhibiting the activity of tryptophan hydroxylase. They are reported to have anxiolytic activity, antagonize the anxiogenic activity of benzodiazepines inverse agonists, reduce chronic abnormally high brain levels of 5 HT or its metabolite 5-hydroxy-indoleacetic acid, and have antibacterial and antiviral activity.

As mentioned previously, it has now been found that certain 3-phenyl-3-aminoalkyl-4-methyl-2,6-dioxopiperidines have a strong analgesic effect. In particular, they have similar potency to morphine and other opioid analgesics but apparently do not act on opioid receptors. They exhibit cross-tolerance with opioid analgesics suggesting that they activate similar physiological systems but via different pharmacological receptors. Accordingly, they are unlikely to exhibit the serious adverse side-effects of opioid agonists and their supply and use may not need to be rigidly controlled.

According to a first aspect of the present invention, there is provided the use in the manufacture of an analgesic medicament of a compound of the following Formula I.

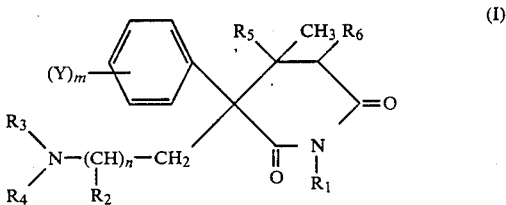

wherein:
$R_1$ represents hydrogen or $C_1$–$C_4$ alkyl;
n is 1 or 2;
$R_2$ represents hydrogen or methyl, provided that one $R_2$ is hydrogen when n is 2;
$R_3$ represents hydrogen or $C_1$–$C_2$ alkyl;
$R_4$ represents $C_1$–$C_2$ alkyl;
$R_5$ and $R_6$ independently represent hydrogen or methyl;
m is 0 to 3; and
each Y is in a meta or para position and independently represents hydroxy, $C_1$–$C_2$ alkoxy, $C_1$–$C_2$ alkyl, $C_1$–$C_2$ hydroxyalkyl, halogen, or trifluoromethyl, provided that hydroxy and alkoxy are not in the para position, or a pharmacologically acceptable salt thereof.

In a second aspect, the invention provides a method of providing an analgesic effect in a patient suffering pain, other than migraine headache, which comprises administering to the patient an analgesic effective amount of a compound of the following Formula I.

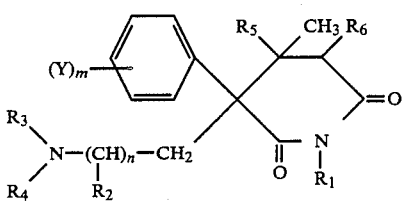

wherein:
$R_1$ represents hydrogen or $C_1$–$C_4$ alkyl;
n is 1 or 2;
$R_2$ represents hydrogen or methyl, provided that one $R_2$ is hydrogen when n is 2;
$R_3$ represents hydrogen or $C_1$–$C_2$ alkyl;
$R_4$ represents $C_1$–$C_2$ alkyl;
$R_5$ and $R_6$ independently represent hydrogen or methyl;
m is 0 to 3; and
each Y is in a meta or para position and independently represents hydroxy, $C_1$–$C_2$ alkoxy, $C_1$–$C_2$ alkyl, $C_1$–$C_2$ hydroxyalkyl, halogen, or trifluoromethyl, provided that hydroxy and alkoxy are not in the para position, or a pharmacologically acceptable salt thereof.

According to a third aspect of the invention, there is provided a topical analgesic composition comprising, in a topical vehicle, a compound of the following Formula I:

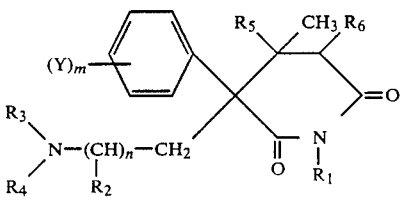

wherein:
$R_1$ represents hydrogen or $C_1$–$C_4$ alkyl;
n is 1 or 2;
$R_2$ represents hydrogen or methyl, provided that one $R_2$ is hydrogen when n is 2;
$R_3$ represents hydrogen or $C_1$–$C_2$ alkyl;
$R_4$ represents $C_1$–$C_2$ alkyl;
$R_5$ and $R_6$ independently represent hydrogen or methyl;
m is 0 to 3; and
each Y is in a meta or para position and independently represents hydroxy, $C_1$–$C_2$ alkoxy, $C_1$–$C_2$ alkyl, $C_1$–$C_2$ hydroxyalkyl, halogen, or trifluoromethyl, provided that hydroxy and alkoxy are not in the para position, or a pharmacologically acceptable salt thereof.

The compounds of Formula I can be used to treat any condition requiring analgesic to suppress pain perception and in particular can be used as a substitute for opioid analgesics. Thus, they can be used for human or veterinary treatment of any painful condition resulting from disease, injury, surgery or any form of trauma. Examples of pain to be treated by the compounds of the invention include chronic pain, intractable pain, pain subject to spontaneous remission, post-operative pain, phantom limb pain, vascular headache, and the like pain. However, treatment of pain associated with migraine headache is excluded from the invention having regard to the previous proposal to use certain of the compounds in the treatment of migraine. It is to be noted that said previous use was not to exploit the analgesic activity of the compounds, which activity was unknown until now.

It also is believed that the compounds of Formula I will be of use in alleviating the symptoms of opioid drug withdrawal.

The compounds of Formula I can be prepared in the manner disclosed in GB 1455687. They exist as optical isomers and can be used in racemate form or as individual (+) or (−) isomers. Presently, the (−) isomer is preferred.

The compounds of Formula I can be administered in various manners to achieve the desired analgesic effect. The compounds can be administered enterally, parenterally, or topically, to the patient being treated. Oral administration is likely to be the preferred route in most circumstances but injection intramuscularly, subcutaneously, intravenously or into other tissue will be preferred in some circumstances. Intrathecal injection directly into the sub or supra arachnoid spaces of the spinal cord may be preferred for presurgical medication, postoperative trauma, childbirth and certain other conditions. Topical application to the skin or the buccal or anal mucosa may be used for local or general pain, inflamation or irritation.

The amount of compound administered will vary and can be any analgesic effective amount. Depending upon the patient and the mode of administration, the quantity of compound administered may vary over a wide range to provide from about 0.01 mg/kg to 20 mg/kg, usually 0.1 mg/kg to 10 mg/kg of body weight of the patient per unit dose. Unit doses of these compounds can contain, for example, from about 1 mg to 500 mg, usually 10 to 100 mg, of the compound and may be administered, for example, from 1 to 4 times daily.

The term "unit dosage form" is used herein to mean a single or multiple dose form containing a quantity of the active ingredient in admixture with or otherwise in association with a diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

The compounds of general Formula I can have the phenyl moiety substituted in one or both meta positions by $C_1$–$C_2$ alkyl, $C_1$–$C_2$ hydroxyalkyl, halogen, trifluoromethyl, or, preferably, hydroxy or $C_1$–$C_2$ alkoxy. Additionally or alternatively, the phenyl moiety can be substituted in the para position by the aforementioned groups other than hydroxy and alkoxy. It is presently preferred that the substituent(s) should be hydroxy or, especially, methoxy. It is also preferred that one or both meta positions are substituted and that, when there are two substituents, they should be the same.

The amino group of the compounds of Formula I can be secondary or tertiary having methyl or ethyl groups attached to the nitrogen atom. Dimethylamino presently is preferred. The amino group is connected to the piperidine ring by a divalent ethylene (i.e. n=1) or trimethylene (i.e. n=2) radical optionally substituted on a carbon atom not adjacent said ring with a methyl group. Presently, unsubstituted trimethylene is preferred.

The piperidine ring of the compounds of Formula I is substituted in the 4-position with methyl and optionally by one or two further methyl groups in the 4 and/or 5 positions. It is presently preferred that there is one further methyl group in the 4 or 5 position, especially in the 4-position.

The ring nitrogen atom of the piperidine ring can be substituted with a $C_1$–$C_4$ alkyl group but it is presently preferred that said nitrogen atom is unsubstituted.

The $C_1$–$C_2$ alkyl groups or moieties referred to herein are methyl or ethyl; methyl presently being preferred. The $C_3$–$C_4$ alkyl groups which may be substituents on the nitrogen atom of the piperidine ring can be straight or branched chain but the straight chain n-propyl or n-butyl groups presently are preferred. The halogen substituent(s) in the phenyl ring can be chlorine, bromine or fluorine; chlorine presently being preferred.

The presently preferred compounds of Formula I are those of the following Formula IA.

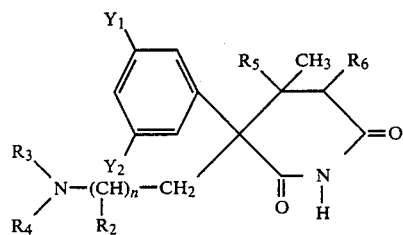

(IA)

wherein:

n is 1 or 2;

$R_2$ represents hydrogen or methyl, provided that one $R_2$ is hydrogen when n is 2;

$R_3$ represents hydrogen or $C_1$–$C_2$ alkyl;

$R_4$ represents $C_1$–$C_2$ alkyl;

$R_5$ and $R_6$ independently represent hydrogen or methyl; and $Y_1$ and $Y_2$ independently represent hydrogen, hydroxy or $C_1$–$C_2$ alkoxy, or a pharmacologically acceptable salt thereof.

The presently especially preferred compounds of Formula 1A are those of the following Formula IB.

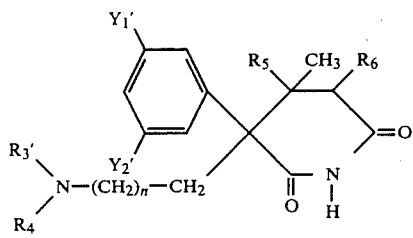

(IB)

wherein:

n is 1 or 2;

$R_3'$ and $R_4$ independently represent $C_1$–$C_2$ alkyl;

$R_5$ and $R_6$ independently represent hydrogen or methyl;

$Y_1'$ represents hydroxy or $C_1$–$C_2$ alkoxy; and $Y_2'$ represents hydrogen, hydroxy or $C_1$–$C_2$ alkoxy, or a pharmacologically acceptable salt thereof.

Examples of compounds of Formula IC include the following:

3-(3'-methoxyphenyl)-3-(2''-N,N-dimethylaminoethyl)-4,4-dimethyl-2,6-dioxopiperidine 3-(3'-methoxyphenyl)-3-(3''-N,N-dimethylaminopropyl)-4,4-dimethyl-2,6-dioxopiperidine (compound 2979—see later);

3-(3'-methoxyphenyl)-3-(2''-N,N-diethylaminoethyl)-4,4-dimethyl-2,6-dioxopiperidine;

3-(3'-methoxyphenyl)-3-(3''-N,N-diethylaminopropyl)-4,4-dimethyl-b 2,6-dioxopiperidine;

3-(3'-hydroxyphenyl)-3-(2''-N,N-dimethylaminoethyl)-4,4-dimethyl-2,6-dioxopiperidine;

3-(3'-hydroxyphenyl)-3-(3''-N,N-dimethylaminopropyl)-4,4-dimethyl-2,6-dioxopiperidine;

3-(3'-methoxyphenyl)-3-(2''-N,N-dimethylaminoethyl)-4,5-dimethyl-2,6-dioxopiperidine;

3-(3'-methoxyphenyl)-3-(3''-N,N-dimethylaminopropyl)-4,5-dimethyl-2,6-dioxopiperidine;

3-(3'-ethoxyphenyl)-3-(3''-N,N-dimethylaminopropyl)-4,4-dimethyl-2,6-dioxopiperidine;

3-(3'-ethoxyphenyl)-3-(3''-N,N-diethylaminopropyl)-4,4-dimethyl-2,6-dioxopiperidine;

3-(3',5'-dimethoxyphenyl)-3-(3''-N,N-dimethylaminopropyl)-4,4-dimethyl-2,6-dioxopiperidine;

3-(3',5'-dimethoxy)-3-(2''-N,N-dimethylaminoethyl)-4,4-dimethyl-2,6-dioxopiperidine;

3-(3',5'-dimethoxy)-3-(3''-N,N-dimethylaminopropyl)-4,5-dimethyl-2,6-dioxopiperidine; and 3-(3',5'-dimethoxy)-3-(2''-N,N-dimethylaminoethyl)-4,5-dimethyl-2,6-dioxopiperidine.

Examples of other compounds of Formula I include:

3-phenyl-3-(2'-N,N-dimethylaminoethyl)-4-methyl-2,6-dioxopiperidine;

3-phenyl-3-(2'-N,N-dimethylaminoethyl)-4,4-dimethyl-2,6-dioxopiperidine;

3-phenyl-3-(2'-N,N-dimethylaminoethyl)-4,5-dimethyl-2,6-dioxopiperidine;

3-phenyl-3(3'-N,N-dimethylaminopropyl)-4,4-dimethyl-2,6-dioxopiperidine;

3-(4'-chlorophenyl)-3(3''-N,N-dimethylaminopropyl)-4,4-dimethyl-2,6-dioxopiperidine; and 3-phenyl-3(2'N-methylaminoethyl)-4,4-dimethyl-2,6-dioxopiperidine.

The compounds of Formula I may be administered in free base form, as an alkali metal or alkaline earth metal salt or as a pharmaceutically acceptable acid addition salt with the proviso that an alkali metal or alkaline earth metal salt is not normally combined with an acid addition salt except in a layer formulation. Representative acid addition salt forms include organic acid salt forms such as the maleate and methane sulphonate and mineral acid salt forms such as the hydrochloride and perchlorate.

The pharmaceutical formulations in which form the active compounds of the invention will normally be utilized are prepared in a manner well known per se in the pharmaceutical art and usually comprise at least one active compound of Formula I in admixture or otherwise in assocation with a pharmaceutically acceptable carrier diluent therefore. For making those formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations may be adapted for enteral or parenteral use and may be administered to the patient in the form of tablets, capsules, dragees, suppositories, syrups, suspensions or the like. Alternatively, the formulations may be adapted for topical application to the skin or mucosal surface and examples of such formulations are ointments, gels, creams, impregnated dressings, sprays or inhalants. The formulations may be in delayed or sustained release form.

Aside from the active agents the compositions may contain pharmaceutically inert organic or inorganic adjuvants, optionally granulating agents, binding agents lubricants, dispersing agents, wetting agents and preservatives. Moreover, the pharmaceutical compositions may contain colouring, flavouring and sweetening substances. Adjuvants for the production of tablets may be e.g. calcium carbonate, lactose micro-crystalline cellulose, mannitol or talc. Starch and alginic acid or microcrystalline cellulose may be used as granulating and disintegrating agents, starch, polyvinylpyrrolidone and gelatine may be used as binding agents and magnesium stearate, stearic acid, colloidal silica and talc as lubricants. Tablet formulation may be coated or uncoated, the coating having the purpose of delaying the disintegration and absorption in the gastrointestinal tract. Suitable suspending agents for the production of liquid administration forms are e.g. methyl cellulose and sodium alginate. Capsule formulation may contain the active agents on their own or together with an inert solid diluent e.g. calcium phosphate, corn starch, lactose, or mannitol.

The invention is illustrated in the following non-limiting Examples.

EXAMPLE 1

Tablet Formulation

Tablets each having the following composition are prepared by conventional techniques:

|  |  | mg/tablet |
|---|---|---|
| (a) | Compound AGN 2979 base | 50 |
| (b) | Lactose | 51.5 |
| (c) | Maize starch dried | 45 |
| (d) | Magnesium stearate | 1.5 |

EXAMPLE 2

Suppository Formulation

|  |  | mg/suppository |
|---|---|---|
| (a) | Compound AGN 2979 HCl | 20 |
| (b) | Oil of Theobroma (cocoa butter) | 980 |

The compound (a) is powdered and passed through a BS No. 100 sieve and triturated with molten oil of Theobroma at 45° C. to form a smooth suspension. The mixture is well stirred and poured into moulds each of nominal 1 G capacity to produce suppositories.

EXAMPLE 3

Tablet Formulation

| (a) | Compound AGN 2979 base | 100 g |
|---|---|---|
| (b) | Wheat starch | 7 g |
| (c) | Lactose | 20 g |
| (d) | Magnesium Stearate | 1 g |

The mixture is compressed into 1000 tablets each weighing 138 mg.

EXAMPLE 4

Pill Formulation

|  |  | per pill |
|---|---|---|
| (a) | Compound AGN 2979 HCl | 50 mg |
| (b) | Corn starch | 45 mg |
| (c) | Liquid glucose | 7 ml |

The pills are prepared by blending the active ingredient (a) and the corn starch, then adding the liquid glucose with thorough kneading to form a plastic mass from which the pills are cut and formed.

EXAMPLE 5

Gelatine Capsule Formulation

|  |  | per capsule |
|---|---|---|
| (a) | Compound AGN 2979 HCl | 50 mg |
| (b) | Talc | 20 mg |

A capsule is prepared by passing dry powdered active ingredient (a) and powdered talc in the above proportions through a fine mesh screen and mixing them well. The powder is then filled into hard gelatin capsules at a net fill of 72.5 mg per capsule.

EXAMPLE 6

Hydrophilic Cream

| Compound AGN 2979 HCl | 25 g |
|---|---|
| Methyl p-hydroxybenzoate | 0.25 g |
| Propyl p-hydroxybenzoate | 0.15 g |
| Sorbitan monostearate | 10 g |
| Propylene Glycol | 120 g |
| Stearyl Alcohol | 250 g |
| White Petroleum Jelly | 250 g |
| Water | 400 ml |

The stearyl alcohol and white petroleum jelly are melted at 75° C. and mixed with an aqueous solution of the other ingredients preheated to 75° C. The mixture is stirred until it congeals and allowed to cool before packing into jars or other containers.

EXAMPLE 7

This Example illustrates the analgesic activity of compounds of Formula I.

Two groups of 5 male Wistar rats were studied. A first rat was placed into a 7 cm diameter glass tube for 1 minute and returned to the home cage for 9 minutes during which time a second rat was placed into the glass tube and the process was repeatedly cycled through 10 rats for more than 2 hours. During the period in the tube, the tail of the rat was laid over a wire coil at room temperature and a low voltage current was then passed through the wire coil sufficient to raise the temperature of the coil by 9.1° C. per second. After approximately 3 seconds, the temperature of the coil reached 42°–45° C. which can be subjectively determined by the experimenter to be a noxious temperature. At about this time the rat flicked the tail away from the coil and the precise latency of the tail-flick was recorded. This latency is a linear index of the temperature which the rat detected as noxious.

When 3 tail-flick latencies had been determined index of the temperature which the rat detected as noxious.

When 3 tail-flick latencies had been determined for each rat, each rat received a coded subcutaneous injection. One group received 2 mg/kg (−) AGN 2979 and one group received 2 mg/kg of morphine. The measurement of tail-flick latencies continued.

The measured tail-flick latencies in seconds is recorded in Tables 1 and 2 below and the results are presented in FIG. 1, which is a graph of average "Index of Analgesia" against time post-injection. The Index of Analgesia was calculated according to the formula:

$$\frac{\text{Tail-flick latency} - \text{control } TFL}{T - \text{control } TFL}$$

where control TFL is the average of the 3 tail-flick latencies of the rat taken before injection of the drug and T is the maximum number of seconds that the experimenter allowed the tail to remain in contact with the coil in the absence of a tail flick reflex (this is necessary to prevent damage to the tail of rats that are insensitive to painful stimuli). The index of analgesia produces data that can be averaged ±s.e. between animals within a group. An index of 0 means no change from control latencies, and an index of 1 means maximum detectable insensitivity to noxious heat.

TABLE 1

(−) AGN 2979
TAIL-FLICK LATENCY (SECONDS)

| TIME* MINUTES | SUBJECT NUMBER | | | | |
|---|---|---|---|---|---|
| | 1 | 2 | 3 | 4 | 5 |
| 0 | 3.6 | 3.5 | 3.1 | 3.4 | 3.4 |
| 10 | 3.1 | 3.4 | 3.2 | 3.1 | 3.4 |
| 20 | 3.3 | 3.3 | 3.3 | 3.0 | 3.5 |
| 30 | 5.3 | 4.4 | 6.0 | 6.0 | 5.0 |
| 40 | 4.9 | 6.0 | 6.0 | 6.0 | 6.0 |
| 50 | 6.0 | 6.0 | 6.0 | 5.7 | 6.0 |
| 60 | 5.9 | 4.9 | 6.0 | 5.9 | 4.9 |
| 70 | 5.9 | 5.2 | 5.3 | 4.7 | 5.5 |
| 80 | 4.7 | 4.6 | 4.9 | 4.9 | 4.8 |
| 90 | 4.6 | 4.4 | 4.7 | 4.2 | 4.7 |
| 100 | 4.1 | 4.5 | 4.9 | 3.9 | 4.2 |
| 110 | 4.1 | 3.7 | 4.0 | 3.5 | 3.5 |
| 120 | 3.7 | 3.4 | 3.6 | 3.2 | 3.3 |

*2 mg/kg (−) AGN 2979 s.c. given at 25 minutes

TABLE 2

MORPHINE
TAIL-FLICK LATENCY (SECONDS)

| TIME* MINUTES | SUBJECT NUMBER | | | | |
|---|---|---|---|---|---|
| | 1 | 2 | 3 | 4 | 5 |
| 0 | 3.2 | 2.9 | 3.1 | 2.8 | 3.4 |
| 10 | 3.1 | 3.4 | 3.3 | 2.9 | 3.1 |
| 20 | 3.3 | 3.2 | 3.4 | 3.0 | 3.2 |
| 30 | 6.0 | 5.2 | 6.0 | 6.0 | 6.0 |
| 40 | 6.0 | 6.0 | 6.0 | 6.0 | 6.0 |
| 50 | 6.0 | 6.0 | 6.0 | 6.0 | 6.0 |
| 60 | 6.0 | 6.0 | 6.0 | 6.0 | 6.0 |
| 70 | 6.0 | 6.0 | 6.0 | 6.0 | 6.0 |

TABLE 2-continued

MORPHINE
TAIL-FLICK LATENCY (SECONDS)

| TIME* MINUTES | SUBJECT NUMBER | | | | |
|---|---|---|---|---|---|
| | 1 | 2 | 3 | 4 | 5 |
| 80 | 6.0 | 6.0 | 6.0 | 6.0 | 6.0 |
| 90 | 5.5 | 6.0 | 6.0 | 6.0 | 5.8 |
| 100 | 4.2 | 5.0 | 4.9 | 5.6 | 4.7 |
| 110 | 3.5 | 4.6 | 3.8 | 4.5 | 4.8 |
| 120 | 3.1 | 3.8 | 3.5 | 4.1 | 3.9 |

*2 mg/kg Morphine s.c. given at 25 minutes

It can be seen from FIG. 1 that a strong analgesic effect was seen in all animals treated with AGN 2979. The peak of the response was delayed until 20 min after the injection and baseline latencies were not recovered until 2 hours after the injection. The potency was of the same order of magnitude as morphine with a similar time course of effect.

EXAMPLE 8

This experiment was conducted in order to establish if AGN 2979 was acting on pharmacological receptors with similar characteristics to those affected by morphine (opioid receptors). Naloxone (i.e. 4,5-epoxy-3,14-dihydroxy-17-(2-propenyl)morphinan-6-one) at a dose of 1 mg/kg is known to prevent drug actions at opioid receptors. Animals were pretreated with this drug but otherwise the procedure was as in Example 7.

Figure 2:
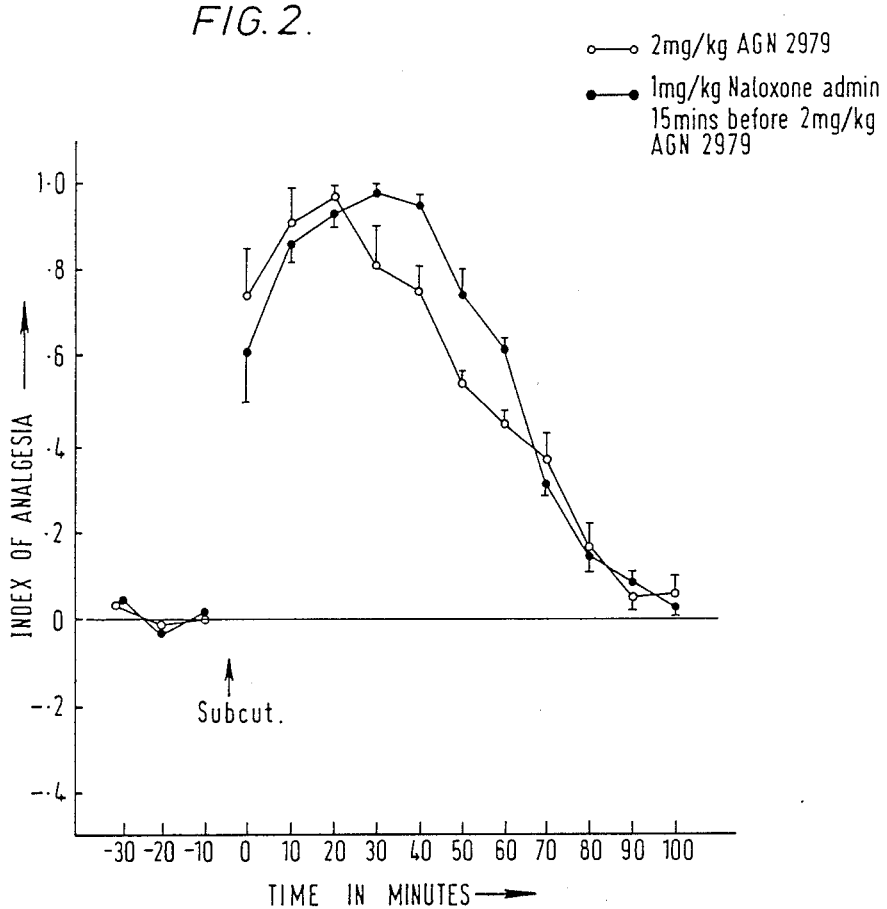

Table 3 gives the tail-flick latency and FIG. 2 shows the Index of Analgesia for the effect of naloxone on the analgesia caused by (−) AGN 2979. It can be seen that naloxone fails to reduce the potency of AGN 2979. This strongly suggests that AGN 2979 does not act on opioid receptors.

TABLE 3

(−) AGN 2979
TAIL-FLICK LATENCY (SECONDS)

| TIME* MINUTES | SUBJECT NUMBER | | | | | |
|---|---|---|---|---|---|---|
| | 1 | 2 | 3 | 4 | 5 | 6 |
| 0 | 3.3 | 3.1 | 3.0 | 3.4 | 3.6 | 3.5 |
| 10 | 3.4 | 3.3 | 3.1 | 3.0 | 3.0 | 2.7 |
| 20 | 3.5 | 3.3 | 2.9 | 3.2 | 3.3 | 3.0 |
| 30 | 5.3 | 5.8 | 4.1 | 4.2 | 5.7 | 4.2 |
| 40 | 6.0 | 6.0 | 5.3 | 5.3 | 5.5 | 5.6 |
| 50 | 6.0 | 6.0 | 5.6 | 5.4 | 6.0 | 5.9 |
| 60 | 6.0 | 6.0 | 6.0 | 5.8 | 6.0 | 6.0 |
| 70 | 5.9 | 6.0 | 5.7 | 5.7 | 6.0 | 6.0 |
| 80 | 5.5 | 6.0 | 4.6 | 5.0 | 5.3 | 5.2 |
| 90 | 4.9 | 5.3 | 4.8 | 4.7 | 5.0 | 4.9 |
| 100 | 4.1 | 4.2 | 4.2 | 4.0 | 4.2 | 3.7 |
| 110 | 3.8 | 3.6 | 3.7 | 3.3 | 4.0 | 3.4 |
| 120 | 3.4 | 3.4 | 3.5 | 3.2 | 3.6 | 3.3 |

*(−) AGN 2979 2 mg/kg s.c. given at 25 minutes following pretreatment with 1 mg/kg i.p. naloxone given at 5 minutes.

Figure 3:
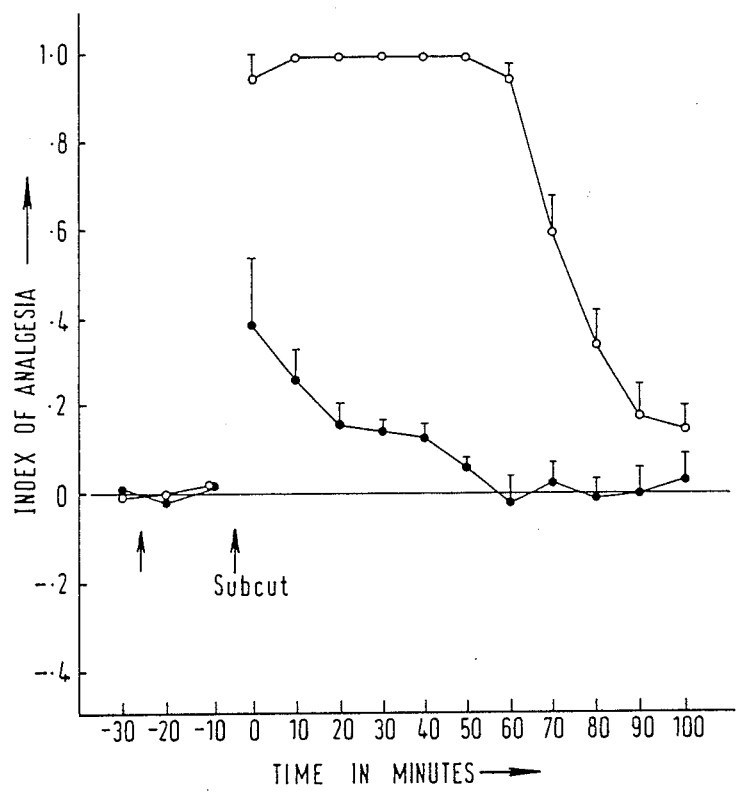

Confirmation that naloxone, at this dose, blocks the analgesic effects of morphine on this test system was sought and the results are shown in Table 4 and FIG. 3. It can be seen that naloxonne very potently reduced the analgesic effects of morphine.

TABLE 4

MORPHINE
TAIL-FLICK LATENCY (SECONDS)

| TIME* MINUTES | SUBJECT NUMBER | | | | |
|---|---|---|---|---|---|
| | 1 | 2 | 3 | 4 | 5 |
| 0 | 3.1 | 3.2 | 3.8 | 3.0 | 3.0 |
| 10 | 3.3 | 3.2 | 3.1 | 2.8 | 3.1 |
| 20 | 3.7 | 3.2 | 3.5 | 2.8 | 3.0 |
| 30 | 6.0 | 3.4 | 4.3 | 3.6 | 4.1 |

TABLE 4-continued

| | MORPHINE TAIL-FLICK LATENCY (SECONDS) | | | | |
|---|---|---|---|---|---|
| TIME* | SUBJECT NUMBER | | | | |
| MINUTES | 1 | 2 | 3 | 4 | 5 |
| 40 | 4.8 | 3.6 | 4.0 | 3.5 | 3.7 |
| 50 | 3.3 | 3.9 | 3.9 | 3.5 | 3.7 |
| 60 | 3.5 | 3.8 | 4.1 | 3.2 | 3.4 |
| 70 | 3.6 | 3.9 | 3.6 | 3.2 | 3.6 |
| 80 | 3.6 | 3.3 | 3.4 | 3.3 | 3.2 |
| 90 | 2.7 | 3.2 | 3.4 | 3.3 | 3.0 |
| 100 | 2.9 | 2.4 | 3.5 | 3.4 | 3.1 |
| 110 | 3.1 | 3.1 | 3.2 | 3.3 | 3.0 |
| 120 | 3.0 | 3.2 | 3.1 | 3.6 | 3.0 |
| 130 | 3.0 | 3.6 | 3.3 | 3.5 | 3.1 |
| 140 | 2.8 | 3.7 | 3.1 | 3.4 | 2.9 |

*Morphine 2 mg/kg s.c. given at 25 minutes following pretreatment with 1 mg/kg i.p. naloxone given at 5 minutes

EXAMPLE 9

One characteristic of drugs acting at opioid receptors is the development of tolerance. If morphine is administered daily then after 7 days or more, depending upon the dosing schedule, morphine has only a very weak analgesic effect (tolerance). Furthermore, all other drugs acting on opioid receptors also have much weaker effects (cross tolerance). This experiment gives rather different information from the experiment with naloxone because it gives insight into the nature of the physiological systems rather than just the pharmacological receptors which are activated by the drugs. If chronic dosing with morphine reduces the level of activity of cells which may be activated by either morphine or another drug, then a cross tolerance experiment will show the interaction between the two. For these reasons cross tolerance between morphine and AGN 2979 was sought.

Animals were given 2 mg/kg s.c. morphine (n=5) or (−) AGN 2979 (n=5) and the tail-flick latencies determined as in Example 6. During the following week, half of these animals received daily s.c. injections of saline and the other half daily doses of morphine. The morphine doses progressively increased according to the schedule 5, 6, 7, 8, 10, 12, 15 mg/kg/day. On the 8th day all animals received s.c. injections identical to those given on the first day of the experiment and the tail-flick latency determined as before.

Figure 4:
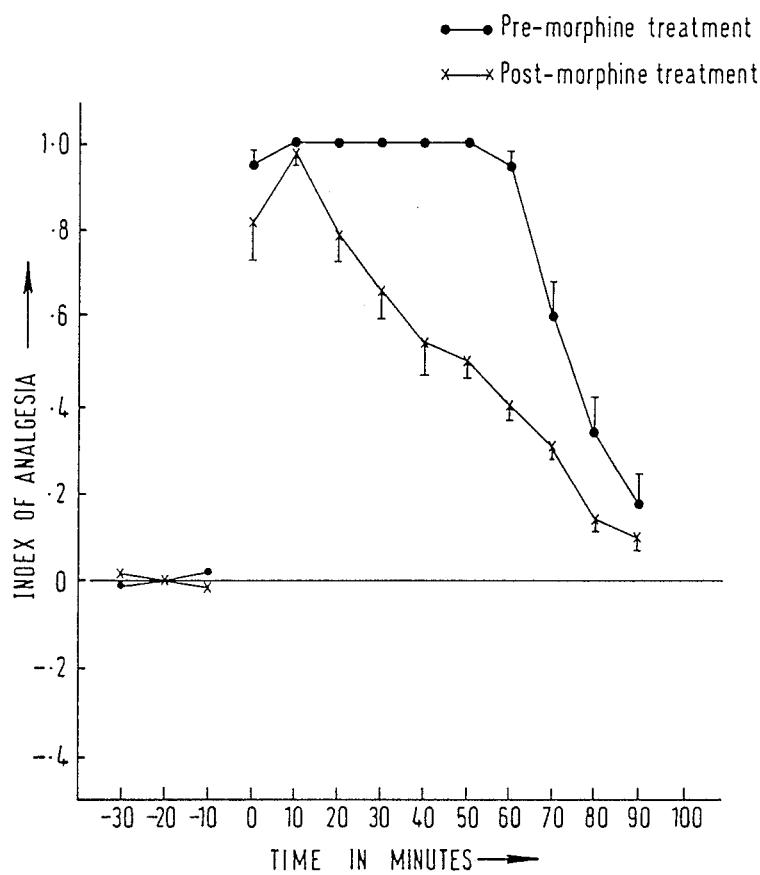
Figure 5:
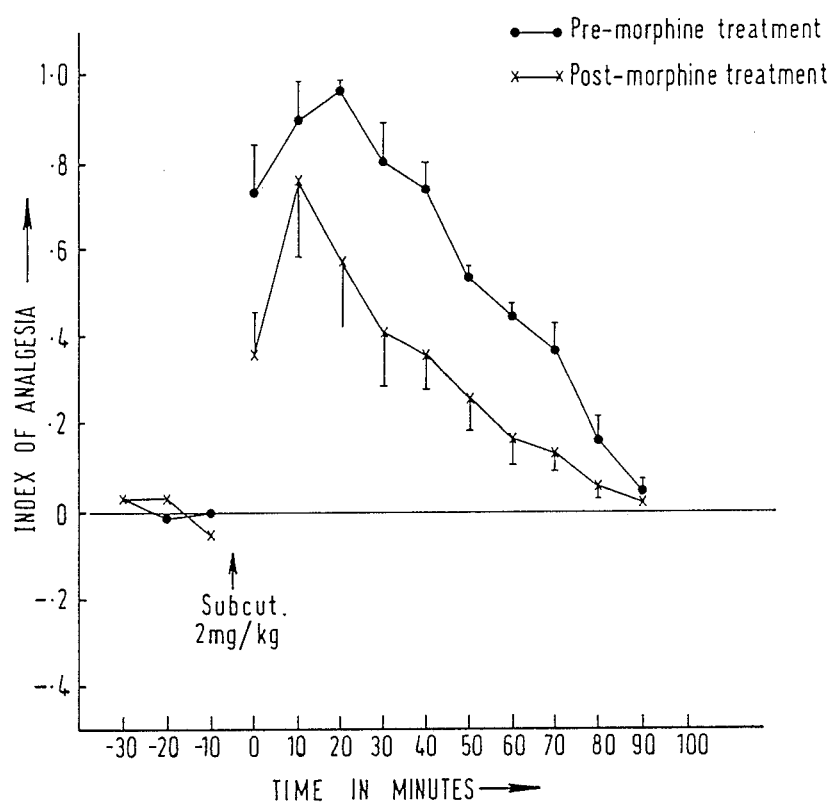

The data are presented in Tables 5 and 6 and FIGS. 4 and 5. It can be seen that on day 1 both morphine and AGN 2979 were potently analgesic and that on day 8 morphine effects were much reduced as was the response to AGN 2979. It is concluded that AGN 2979 does show cross tolerance with morphine indicating that it acts via a similar physiological system to morphine although via a different receptor.

TABLE 5

| | (−) AGN 2979 TAIL-FLICK LATENCY (SECONDS) | | | | |
|---|---|---|---|---|---|
| TIME* | SUBJECT NUMBER | | | | |
| MINUTES | 1 | 2 | 3 | 4 | 5 |
| 0 | 0.0 | 0.4 | 3.2 | 3.0 | 3.3 |
| 10 | 3.5 | 3.3 | 3.4 | 3.2 | 3.2 |
| 20 | 3.3 | 3.1 | 2.9 | 3.0 | 3.1 |
| 30 | 3.3 | 4.2 | 4.9 | 4.6 | 4.1 |
| 40 | 5.9 | 5.7 | 6.0 | 6.0 | 3.4 |
| 50 | 4.6 | 5.5 | 5.3 | 5.5 | 3.3 |
| 60 | 4.2 | 4.7 | 4.9 | 4.8 | 3.2 |
| 70 | 4.3 | 4.4 | 4.7 | 4.2 | 3.5 |
| 80 | 4.0 | 4.0 | 4.5 | 3.8 | 3.4 |

TABLE 5-continued

| | (−) AGN 2979 TAIL-FLICK LATENCY (SECONDS) | | | | |
|---|---|---|---|---|---|
| TIME* | SUBJECT NUMBER | | | | |
| MINUTES | 1 | 2 | 3 | 4 | 5 |
| 90 | 3.9 | 3.7 | 4.2 | 3.5 | 3.2 |
| 100 | 4.1 | 3.4 | 3.5 | 3.4 | 3.6 |
| 110 | 3.6 | 3.5 | 3.1 | 3.2 | 3.5 |
| 120 | 3.4 | 3.3 | 3.2 | 3.1 | 3.4 |
| 130 | 3.2 | 3.1 | 3.0 | 3.0 | 3.3 |
| 140 | 3.0 | 3.1 | 2.8 | 3.1 | 3.1 |

*(−) AGN 2979 2 mg/kg s.c. given at 25 mintues following the development of tolerance by repeated administration of morphine for seven days

TABLE 6

| | MORPHINE TAIL-FLICK LATENCY (SECONDS) | | | | |
|---|---|---|---|---|---|
| TIME* | SUBJECT NUMBER | | | | |
| MINUTES | 1 | 2 | 3 | 4 | 5 |
| 0 | 3.0 | 3.2 | 3.1 | 3.5 | 3.3 |
| 10 | 3.1 | 3.4 | 3.2 | 3.4 | 3.0 |
| 20 | 3.2 | 3.3 | 3.0 | 3.2 | 3.2 |
| 30 | 5.1 | 4.7 | 6.0 | 6.0 | 5.8 |
| 40 | 6.0 | 5.8 | 6.0 | 6.0 | 6.0 |
| 50 | 5.1 | 5.1 | 5.6 | 6.0 | 5.3 |
| 60 | 4.9 | 5.1 | 4.7 | 5.8 | 4.8 |
| 70 | 5.2 | 4.8 | 4.0 | 5.1 | 4.5 |
| 80 | 4.9 | 4.6 | 4.2 | 4.8 | 4.6 |
| 90 | 4.6 | 4.1 | 4.1 | 4.5 | 4.4 |
| 100 | 4.2 | 4.0 | 3.9 | 4.3 | 4.0 |
| 110 | 3.5 | 3.8 | 3.6 | 3.5 | 3.7 |
| 120 | 3.4 | 3.5 | 3.7 | 3.3 | 3.6 |
| 130 | 3.3 | 3.4 | 3.5 | 3.2 | 3.3 |
| 140 | 3.1 | 3.3 | 3.2 | 3.2 | 3.1 |

*Morphine 2 mg/kg s.c. given at 25 mintues following the development of tolerance by repeated administration of morphine for seven days.

I claim:

1. A method for the analgesic treatment of pain, other than migraine headache, which comprises administering to a patient suffering pain an analgesic effective amount of a compound of the following Formula I

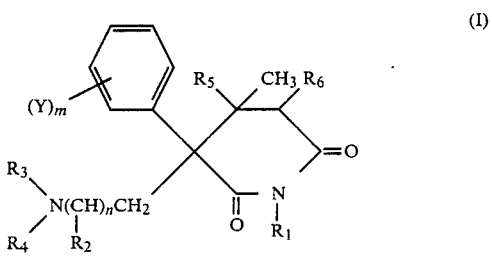

wherein:
$R_1$ represents hydrogen or $C_1$-$C_4$ alkyl;
n is 1 or 2;
$R_2$ represents hydrogen or methyl, provided that one $R_2$ is hydrogen when n is 2;
$R_3$ represents hydrogen or $C_1$-$C_2$ alkyl;
$R_4$ represents $C_1$-$C_2$ alkyl;
$R_5$ and $R_6$ independently represent hydrogen or methyl;
m is 0 to 3; and
each Y is in a meta or para position and independently represents hydroxy, $C_1$-$C_2$ alkoxy, $C_1$-$C_2$ alkyl, $C_1$-$C_2$ hydroxyalkyl, halogen, or trifluoromethyl, provided that hydroxy and alkoxy are not in the para position,
or a pharmacologically acceptable salt thereof.

2. The method according to claim 1, wherein the compound has the following Formula IA

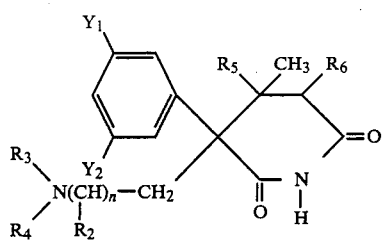
(IA)

wherein:
 n is 1 or 2;
 R$_2$ represents hydrogen or methyl, provided that one R$_2$ is hydrogen when n is 2;
 R$_3$ represents hydrogen or C$_1$-C$_2$ alkyl;
 R$_4$ represents C$_1$-C$_2$ alkyl;
 R$_5$ and R$_6$ independently represent hydrogen or methyl; and
 Y$_1$ and Y$_2$ independently represent hydrogen, hydroxy or C$_1$-C$_2$ alkoxy,
or a pharmacologically acceptable salt thereof.

3. The method according to claim 2, wherein the compound has the following Formula IB

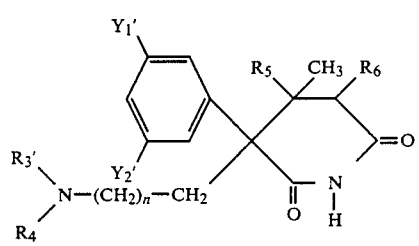
(IB)

wherein:
 n is 1 or 2;
 R$_3$' and R$_4$ independently represent C$_1$-C$_2$ alkyl;
 R$_5$ and R$_6$ independently represent hydrogen or methyl;
 Y$_1$' represents hydroxy or C$_1$-C$_2$ alkoxy; and
 Y$_2$' represents hydrogen, hydroxy or C$_1$-C$_4$ alkoxy,
or a pharmacologically acceptable salt thereof.

4. The method according to claim 3, wherein the compound is 3-(3'-methoxyphenyl)-3-(3''-N,N-dimethylaminopropyl)-4,4-dimethyl-2,6-dixopiperidine.

5. The method according to claim 4, wherein the compound is the minus isomer.

6. The method according to claim 1, wherein the said analgesic effective amount is about 0.01 mg/kg to about 20 mg/kg.

7. The method according to claim 6, wherein the said analgesic effective amount is about 0.1 mg/kg to about 10 mg/kg.

8. A topical analgesic composition comprising, in a topical vehicle, a compound of the following Formula I

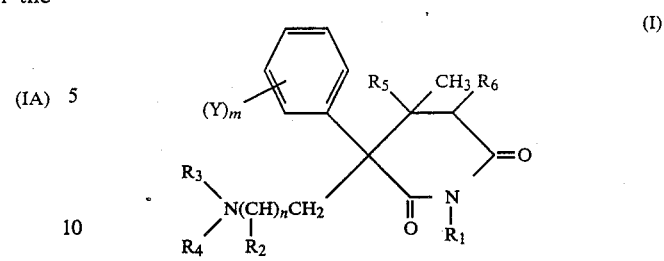
(I)

wherein:
 R$_1$ represents hydrogen or C$_1$-C$_4$ alkyl;
 n is 1 or 2;
 R$_2$ represents hydrogen or methyl, provided that one R$_2$ is hydrogen when n is 2;
 R$_3$ represents hydrogen or C$_1$-C$_2$ alkyl;
 R$_4$ represents C$_1$-C$_2$ alkyl;
 R$_5$ and R$_6$ independently represent hydrogen or methyl;
 m is 0 to 3; and
 each Y is in a meta or para position and independently represents hydroxy, C$_1$-C$_2$ alkoxy, C$_1$-C$_2$ alkyl, C$_1$-C$_2$ hydroxyalkyl, halogen, or trifluoromethyl, provided that hydroxy and alkoxy are not in the para position,
or a pharmacologically acceptable salt thereof.

9. The composition according to claim 8, wherein the compound has the following Formula IA

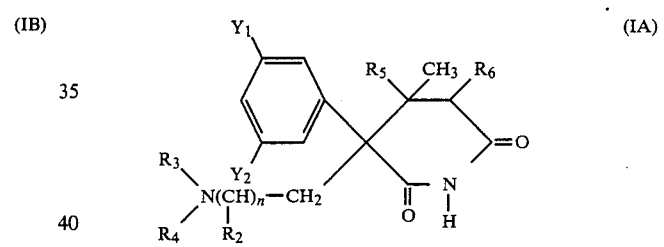
(IA)

wherein:
 n is 1 or 2;
 R$_2$ represents hydrogen or methyl, provided that one R$_2$ is hydrogen when n is 2;
 R$_3$ represents hydrogen or C$_1$-C$_2$ alkyl;
 R$_4$ represents C$_1$-C$_2$ alkyl;
 R$_5$ and R$_6$ independently represent hydrogen or methyl; and
 Y$_1$ and Y$_2$ independently represent hydrogen, hydroxy or C$_1$-C$_2$ alkoxy,
or a pharmacologically acceptable salt thereof.

10. The composition according to claim 9, wherein the compound has the following Formula IB

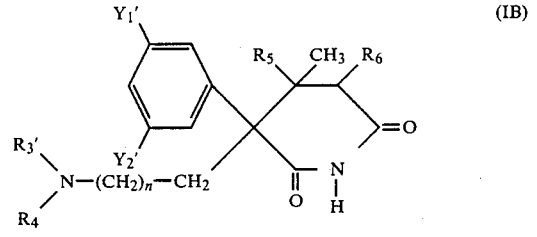
(IB)

wherein:
 n is 1 or 2;

$R_3'$ and $R_4$ independently represent $C_1$–$C_2$ alkyl;

$R_5$ and $R_6$ independently represent hydrogen or methyl; and $Y_1$ and $Y_2$ independently represent hydrogen, hydroxy or $C_1$–$C_2$ alkoxy, or a pharmacologically acceptable salt thereof.

11. The composition according to claim 10, wherein the compound is 3-(3'-methoxyphenyl)-3-(3''-N,N-dimethylaminopropyl)-4,4-dimethyl-2,6-dixopiperidine.

12. The composition according to claim 11 wherein the compound is the minus isomer.

13. The composition according to claim 8 which is an ointment, gel or cream.

14. The composition according to claim 8 which is an impregnated dressing.

15. The composition according to claim 8 which is a spray or inhalant.

* * * * *